United States Patent [19]

Kakeya et al.

[11] 4,189,479

[45] Feb. 19, 1980

[54] CEPHALOSPORIN ESTERS

[75] Inventors: Nobuharu Kakeya, Kawanishi; Yoshinobu Yoshimura, Suita, both of Japan

[73] Assignee: Takeda Chemical Industries, Ltd., Japan

[21] Appl. No.: 863,071

[22] Filed: Dec. 22, 1977

[51] Int. Cl.[2] .................................... C07D 501/36
[52] U.S. Cl. ..................................... 424/246; 544/27
[58] Field of Search ........................... 544/27; 424/246

[56] References Cited

U.S. PATENT DOCUMENTS

| 4,080,498 | 3/1978 | Numata et al. .................. 424/246 |
| 4,146,710 | 3/1979 | Naito et al. ..................... 544/27 |

*Primary Examiner*—Nicholas S. Rizzo
*Attorney, Agent, or Firm*—Craig and Antonelli

[57] ABSTRACT

Novel cephalosporin derivatives, namely pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate and its pharmaceutically acceptable acid addition salts are found to be useful as orally administrable antibiotics having broad antimicrobial activities against both gram-positive and gram-negative bacteria.

8 Claims, No Drawings

CEPHALOSPORIN ESTERS

This invention relates to a novel cephalosporin derivative and an orally administrable pharmaceutical composition containing the same. More particularly, this invention pertains to pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate and its acid addition salts and also to an orally administrable pharmaceutical composition containing said compound or a pharmaceutically acceptable acid addition salt thereof as effective ingredient.

Extensive studies made by the present inventors led to the following findings, namely the above-mentioned cephalosporin derivative (hereinafter sometimes referred to as "ester compound") and its acid addition salts are readily absorbed into body through gastrointestinal tract and they are hydrolyzed under the influence of the enzymes present in the host to the corresponding free carboxylic acid compound (hereinafter sometimes referred to as "non-ester compound"), which has antibacterial activity against both gram-positive and gram-negative bacteria including such ones as having acquired resistance against so far known cephalosporanic antibiotics, thereby the concentration of the non-ester compound in blood reaches a high level enough to show the therapeutic effect, and therefore the ester compound and its acid addition salts are useful as an orally administrable antibiotics having a very broad anti-microbial spectrum.

The above-mentioned acid addition salts are formed at the aminothiazol group and/or dimethylamino group of the ester compound, thereby the properties such as water-solubility, absorption efficiency and stability, of the ester compound may be further improved. As preferable acids suitable for forming such acid addition salts, there may be mentioned well-known acids for forming pharmaceutically acceptable salts in the field of penicillins and cephalosporins. Namely, they include mineral acids such as hydrochloric acid, sulfuric acid, phosphoric acid and the like, and organic acids such as maleic acid, acetic acid, citric acid, succinic acid, tartaric acid, benzoic acid, fumaric acid, malonic acid, mandelic acid, ascorbic acid and the like.

The ester compound of the present invention and its acid addition salts can be produced by per se known methods. For example, they can be produced by esterifying the non-ester compound or its salt with a compound of the formula:

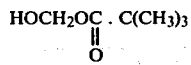

or its reactive derivatives. As said reactive derivatives, there may be used per se known derivatives, especially, esterification by means of a compound of the formula:

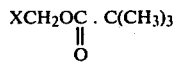

(wherein X is a halogen atom) is preferable. The salts of the non-ester compound may be exemplified by acid addition salts with mineral acids such as hydrochloric acid, sulfuric acid or nitric acid, or organic acids such as oxalic acid or p-toluene sulfonic acid, or salts with alkali metals such as sodium or potassium, alkali earth metals such as calcium or magnesium or bases such as triethyl amine, trimethylamine, pyridine, colidine or lutidine. As halogen atom, any of chlorine, bromine and iodine may be used. From standpoint of reactivity iodine and bromine are preferable, the former being most preferred.

The esterification reaction is generally carried out in a solvent inert to the reaction. As such solvents, there may be mentioned amides, ketones, nitriles, liquefied sulfurous acids and so on. Typical examples of these solvents are acetonitrile, N,N-dimethylformamide(DMF), N,N-dimethylacetamide (DMA), dichloromethane, chloroform, dimethylsulfoxide(DMSO), diethylether, dioxane, tetrahydrofuran(THF), acetone, methyl ethyl ketone, etc. Among them, DMF, acetone, acetonitrile and liquefied sulfurous acid anhydride are particularly preferred. The reaction may preferably be carried out in the presence of a base. Any base capable of acting as deacidation agent can be used. For example, there may be used organic amines such as dicyclohexylamine, N-ethyl aniline, morpholine, N,N-diethyl aniline, N-methyl morpholine, pyridine, triethylamine, etc. or inorganic bases such as sodium hydrogen carbonate, lithium carbonate or potassium hydrogen carbonate. The amount of the base to be used is desirably not less than equimolar to the non-ester compound or its salt. The esterification reaction is carried out generally at a temperature in the range from −° to 20° C. When liquefied sulfurous acid anhydride is used as a solvent, the reaction is carried out preferably at a temperature near the boiling point of this solvent (−10° C.), namely at −10° to −20° C. The reaction time may differ, depending on the reactants and the solvent employed, but is generally in the range from about 10 minutes to about 6 hours. The reaction product can be isolated and purified by per se known methods such as solvent extraction, pH adjustment, phase transfer, crystallization, recrystallization, chromatography, etc.

When free ester compound is obtained by the method as described above, it may be converted to a pharmaceutically acceptable salt or alternatively, when the compound is obtained in the form of a salt, it may be converted to a free form, by per se known methods, respectively. Further, the aminothiazole group in the above compounds may sometimes be present as tautomer, i.e. iminothiazolin group.

The thus produced ester compound or a pharmaceutically acceptable acid addition salt thereof is diluted with diluents for medicines by per se known methods to prepare an orally administrable cephalosporin medicament of the present invention. Dilution may be carried out by conventional methods known per se such as mixing. Examples of suitable diluents are starch, lactose, sucrose, calcium carbonate, calcium phosphate and the like. There may also be compounded, if desired, with other additives. Preferable additives are, for example, binders (e.g. starch, gum arabic, carboxymethyl cellulose, hydroxypropyl cellulose or crystalline cellulose), lubricants (e.g. magnesium stearate or talc) or disintegrators (e.g. carboxymethyl calcium or talc). After various components are mixed, the mixture is made into various forms suitable for oral administration by per se known methods such as capsules, dispersants, fine particles, granules or dry syrup.

The orally administrable cephalosporin preparations of the present invention can be used as an antibiotic having broad spectrum for oral administration for treatment of infections diseases caused by various gram-positive and gram-negative bacteria. When the preparation of the present invention is orally administered the ester compound or a salt thereof is absorbed from gastrointestinal tract and hydrolyzed immediately by enzymes in a body to be converted to corresponding non-ester compound or a salt thereof. The non-ester compound and its salts have especially excellent anti-microbial activity. Namely, said non-ester compound and its salt exhibit excellent anti-microbial activities against gram-positive bacteria such as *Staphylococcus aureus*, and gram-negative bacteria such as *Escherichia coli, Klebsiella pneumoniae, Proteus vulgaris, Proteus mirabilis* and *Proteus morganii*. Further, the ester compound and its salts are low in toxicity. Accordingly, the cephalosporin preparations of the present invention can be used as effective orally administrable antibiotics for treatment of various diseases caused by these bacteria.

More specifically, the cephalosporin preparation of the present invention can be used for treatment of, for example, pyogenic diseases, biliary tract, respiratory and urinary tract infections caused by the aforesaid bacteria in human beings and other warm-blooded animals (e.g. rat, mouse, rabbit, horse, dog, monkey, etc.). The cephalosporin preparation of the present invention may be administered by oral route, for example, in case of pyogenic disease in adult human, at a dosage of about 3 to 4 times administrations in a dose of about 1 to 20 mg/kg-body weight per every administration, calculated as non-ester compound.

The present invention is described in further detail by referring to the following Examples, by which the present invention is not limited.

EXAMPLE 1

Preparation of pivaloyloxymethyl 7β-[( 2-(2-amino-thiazol-4-yl)acetamido]-3-[[[1-(2-dimethylaminoethyl)-1H-tetrazol-5-yl]thio]methyl]-ceph-3-em-4-carboxylate:

In 60 ml of dimethylformamide, there is dissolved 5.9 g of potassium 7β-[2-(2-aminothiazol-4-yl)acetamido]-3-[[[1-(2-dimethylaminoethyl)-1H-tetrazol-5-yl]thio]methyl]-ceph-3-em-4-carboxylate. While stirring the mixture under ice-cooling, a solution of 2.4 g pivaloyloxymethyl iodide in 5 ml dimethylformamide is added dropwise for 10 minutes. After the mixture is stirred for additional 20 minutes, the reaction mixture is mixed with ethyl acetate (1 l) and washed with water (150 ml×4), then with a saturated aqueous sodium chloride solution (100 ml×2), and dried over anhydrous sodium sulfate. This solution is concentrated under reduced pressure to give white powders, which are washed out with ethyl ether, followed by suction filtration, and dried under reduced pressure to obtain the objective compound.

Yield 4.2 g, m.p. 84°–87° C.

IR(KBr cm−): 1780, 1735

NMR(90 MHz, in d6-DMSO, δ): 1.17(s,(CH3)3C), 2.16(s,N(CH3)2, 2.65(t,J=6Hz,NCH2), 3.35(s,2—CH2), 4.18 and 4.46(ABq,J=15Hz,3-CH2), 4.33(t,J=6Hz,NCH2), 5.06(d,J=5Hz,6-H), 5.6–5.9(m,7-H and, O—CH2—O), 6.20(s,thiazole—5H), 6.76(broad s, —NH2), 8.82(d,J=7.5Hz, CONH)

Elemental analysis:
Calculated for C24H33N9O6S3.1/2H2O: C, 44.41; H, 5.24; N, 19.42;
Found: C, 44.53; H, 5.11; N, 19.16.

This product (1.0 g) is dissolved in 100 ml of ethyl acetate and mixed with ethereal dry hydrochloric acid to precipitate white powders. After suction filtration under reduced pressure, the powders are dried to obtain di-hydrochloride of the title compound.

Yield: 630 mg

IR(KBr, cm−1): 1770, 1735,

NMR(90 MHz, in D2O, δ): 1.21(s,(CH3)3C), 3.08(s, N(CH3)2), 3.7–4.5(m,N(CH2) and 2-CH2), 4.97(t,J=7Hz,

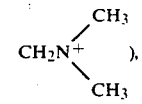

5.20(d,J=4.5Hz,6H), 5.68–5.85(m,O-CH2-O), 5.93(d,J=4.5Hz), 6.71(s,thiazole-5H)

Elemental analysis:
Calculated for C24H33N9O6S3.2HCl.H2O: C, 39.45; H, 5.06; N, 17.26,
Found: C, 39.50; H, 5.28; N, 16.46.

EXAMPLE 2

Various pharmaceutical compositions are prepared according to the following procedures.

(1) The principal medicine and lactose are previously mixed and to the resultant mixture is added a 10% aqueous hydroxypropyl cellulose solution. The mixture is kneaded, then dried and crushed to prepare particles. The particles are mixed with magnesium stearate previously dispersed in starch and molded into tablets having the composition as below.

| | |
|---|---|
| Pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate | 76.0 mg |
| Lactose | 16.0 mg |
| Starch | 5.0 mg |
| Hydroxypropyl cellulose | 2.7 mg |
| Magnesium stearate | 0.3 mg |
| | 100 mg/tablet |

Similar tablets are prepared by repeating the above procedure except that the above principal medicine is replaced by its hydrochloric acid salt.

(2) (a) A mixture of a part of starch and magnesium stearate is blended with the principal medicine and residual starch. The resultant blend is made into capsules by conventional encapsulation method, the composition of which is as below.

| | |
|---|---|
| Pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate | 76 mg |
| Starch | 22 mg |
| Magnesium stearate | 2 mg |
| | 100 mg/capsule |

(b) By the same method as described in (a), capsules are prepared from the following composition:

| | |
|---|---|
| Pivaloyloxymethyl 7β-[2-(2-aminothiazol-4-yl)acetamido]-3-3-[[[1-(2-dimethylaminoethyl)-1H-tetrazol-5-yl]thio]methyl]- | |

| -continued | | |
|---|---|---|
| ceph-3-em-4-carboxylate dihydrochloride | 84.7 | mg |
| Starch | 37.3 | mg |
| Magnesium stearate | 3 | mg |
| | 125 | mg/capsule |

(3) The principal medicine, starch and lactose are previously mixed and then kneaded with a 10% aqueous hydroxypropyl cellulose solution, followed by drying and crushing to prepare particles, which are then separated by a sieve into fine particles with sizes of 32 to 150 mesh, whose composition is as below.

| | |
|---|---|
| Pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate | 76 mg |
| Lactose | 12 mg |
| Starch | 9 mg |
| Hydroxypropyl cellulose | 3 mg |
| | 100 mg |

Similar fine particles are obtained by using corresponding hydrochloride in place of the principal medicine in the above composition.

(4) Particles are prepared by the same method as in (3) and separated by a sieve into granules with sizes of 12 to 48 mesh, whose composition is as below.

| | |
|---|---|
| Pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate | 76 mg |
| Lactose | 16 mg |
| Starch | 4 mg |
| Hydroxypropyl cellulose | 4 mg |
| | 100 mg |

(5) The principal medicine, sucrose, citric acid anhydride and 0.5 ml of water are kneaded, followed by drying and crushing, to prepare a dry syrup having the following composition.

| | |
|---|---|
| Pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate | 76 mg |
| Sucrose | 90 mg |
| Citric acid anhydride | 10 mg |
| | 176 mg |

In place of the above principal medicine, corresponding hydrochloride is used to prepare similar dry syrup.

EXAMPLE 3

Acute toxicity test

The cephalosporin preparations of the present invention are administered orally to mouse and rat to examine acute toxicity to give the following results.

Subject: 5 male mice (ICR strain 5 weeks old) 5 male rats (SD strain 5 weeks old)
Method: The ester compound obtained in Example 1 is made into a 5% gum arabic suspension and administered orally to the animals in doses of 0.5 to 3.0 g/kg. The amount of liquid is 0.2 ml/10 g-body weight.
Observation Term: 7 days
Result: $LD_{50}$(g/kg)
Mouse —>3.0
Rat —>3.0

EXAMPLE 4

Oral administration test

The cephalosporin preparations of the present invention are administered orally to human being to give the results of blood level of the non-ester compound and urinary recovery as shown below.

Subject: 3 Healthy adult human volunteers
Dose: The ester compound obtained in Example 1: 152 mg, or dihydrochloride of the ester compound: 169.4 mg, each corresponding to 125 mg of the non-ester compound.
Method of administration: Two capsules of (2) (a) or (b) in Example 2 are orally administered.
Quantitative method: Proteus mirabilis is used as the bacteria to be examined and quantitative analysis is conducted by cylinder-plate assay.

| | Blood-level (mcg/ml: average of three samples) Time (hours) | | | |
|---|---|---|---|---|
| | 0.5 | 1 | 2 | 4 |
| Capsule of Example 2 (2) (a) (ester compound) | 1.20 | 4.0 | 2.1 | 0.30 |
| Intramuscular administration of non-ester compound (reference) *1 | 6.33 | 4.80 | 2.1 | 0.43 |

| | Urinary recovery (%) 0-6 hours: average of three samples |
|---|---|
| Capsule of Example 2 (2) (a) (ester compound) | 51.5 |
| Capsule of Example 2 (2) (b) (ester compound dihydrochloride) | 50.5 |
| Intramuscular administration of non-ester compound (reference) *1 | 68.0 |

*1 dose: 125 mg

The ester compound after being absorbed is hydrolyzed at 4-position carboxylic acid ester and found to exist in either blood or urine as non-ester compound of the corresponding 4-position carboxylic acid of the cephalosporin compound.

What we claim is:

1. Pivaloyloxymethyl 7β-[2-(2-aminothiazol-4-yl)-acetamido]-3-[[[1-(2-dimethylaminoethyl)-1H-tetrazol-5-yl]thio]methyl]-ceph-3-em-4-carboxylate or its pharmaceutically acceptable acid addition salt.

2. The compound according to claim 1, wherein the acid addition salt is hydrochloride.

3. The compound according to claim 1, which is pivaloyloxymethyl 7β-[2-(2-aminothiazol-4-yl)acetamido]-3-[[[1-(2-dimethylaminoethyl)-1H-tetrazol-5-yl]methyl]-ceph-3-em-4-carboxylate dihydrochloride.

4. The compound according to claim 1, which is pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate.

5. A pharmaceutical composition comprising pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate or its pharmaceutically acceptable acid addition salt as an effective ingredient.

6. The pharmaceutical composition according to claim 5, wherein the acid addition salt is hydrochloride.

7. The pharmaceutical composition according to claim 5, wherein the effective ingredient is pivaloyloxymethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate dihydrochloride.

8. The pharmaceutical composition according to claim 5, wherein the effective ingredient is pivaloyloxymethyl 7β-[2-(2-aminothiazol-4-yl)acetamido]-3-[[[-1-(2-dimethylaminoethyl)-1H-tetrazol-5-yl]thio]methyl]-ceph-3-em-4-carboxylate.

* * * * *